United States Patent
Lueck

(10) Patent No.: US 9,333,149 B2
(45) Date of Patent: *May 10, 2016

(54) POLYMERIZABLE DENTAL MATERIAL

(71) Applicant: Muhlbauer Technology GmbH, Hamburg (DE)

(72) Inventor: Rainer Lueck, Tornesch (DE)

(73) Assignee: MUHLBAUER THECHNOLOGY GMBH, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/510,926

(22) Filed: Oct. 9, 2014

(65) Prior Publication Data

US 2015/0094397 A1 Apr. 2, 2015

Related U.S. Application Data

(63) Continuation of application No. 12/308,309, filed as application No. PCT/EP2007/004207 on May 11, 2007, now Pat. No. 8,883,876.

(30) Foreign Application Priority Data

Jun. 30, 2006 (EP) ..................................... 06013589

(51) Int. Cl.
*A61K 6/08* (2006.01)
*A61F 2/00* (2006.01)
*A61K 6/083* (2006.01)
*A61K 6/00* (2006.01)
*A61K 6/027* (2006.01)

(52) U.S. Cl.
CPC ............... *A61K 6/083* (2013.01); *A61K 6/0017* (2013.01); *A61K 6/0023* (2013.01); *A61K 6/0038* (2013.01); *A61K 6/0276* (2013.01)

(58) Field of Classification Search
CPC ...................................................... A61K 6/083
USPC ........................................................ 523/116
See application file for complete search history.

(56) References Cited

U.S. PATENT DOCUMENTS

| | | | |
|---|---|---|---|
| 4,923,400 A | 5/1990 | Suzuki et al. | |
| 5,376,691 A | 12/1994 | May et al. | |
| 5,688,883 A | 11/1997 | Klee et al. | |
| 5,707,611 A | 1/1998 | Ikemura et al. | |
| 5,922,786 A | 7/1999 | Mitra et al. | |
| 5,977,199 A | 11/1999 | Xie et al. | |
| 6,288,138 B1 | 9/2001 | Yamamoto et al. | |
| 6,583,197 B1 | 6/2003 | Wada et al. | |
| 6,852,775 B1 | 2/2005 | Soglowek et al. | |
| 7,041,164 B2 | 5/2006 | Kanca | |
| 7,132,461 B2 | 11/2006 | O'Leary et al. | |
| 7,214,726 B2 | 5/2007 | Qian | |
| 7,879,924 B2 | 2/2011 | Torii et al. | |
| 8,236,871 B2 | 8/2012 | Hecht et al. | |
| 8,883,876 B2 | 11/2014 | Lueck et al. | |
| 2005/0014861 A1* | 1/2005 | Qian ................... | A61K 6/0017 523/116 |

FOREIGN PATENT DOCUMENTS

| | | |
|---|---|---|
| DE | 975072 | 8/1961 |
| EP | 0923924 | 6/1999 |
| JP | 05-295013 | 11/1993 |

OTHER PUBLICATIONS

Bredereck et al., "Uber CH-Aktive Polymerisationsintiatoren—XIII. Mitt. Polymerisationen und Polymerisationsintiatoren." ["CH-Active Polymerization Intiators—XIIIth Communication. Polymerizations and Polymerizatio Initiatoes."], *Makromolekulare Chemie*, 92:70-90 (1966).
Bredereck et al., "Polymerisationen und Polymerisationsintiatoren—16. Einflu.beta. Von Thio-Gruppen in Barbitursaurederivaten auf die Polymerisationsauslosung von Methacrylsaure-methylester." ["Polymerizations and Polymerization Initiatoes—16. Influence of Thio Groups in Barbituric Acid Derivatives on the Initiation of the Polymerization of Methyl Methacrylate."], Makromolekulare Chemie, 176:1713-1723 (1975).
Cope et al., "1,3-Dimethyl-5-alkyl Barbituric Acids." J. Amer Chem Soc 63:365 (1941).
Fischer et al., "Uber c-Dialkylbarbitursauren and uber die Ureide der Dialkylessigsauren." ["C-Dialkylbarbituric Acids and the Ureides of Dialkylacetic Acids."], Ann der Chemie, 335:335 (1904).
Schmit, "Kaltpolymerisate: Ein Bericht uber ihre Eigenschaften, Einsatzmoglichkeiten und Vorteile," ["Cold polymers: A report on their Porperties, Possible Uses and Advantages."], pp. 17-22 (1970).
International Search Report for PCT/EP2007/004207 dated Sep. 5, 2007, 4 pages.

* cited by examiner

*Primary Examiner* — David Karst
(74) *Attorney, Agent, or Firm* — Casimir Jones, S.C.; Mary Ann D. Brow

(57) ABSTRACT

The subject matter of the invention is a radically polymerizable dental material comprising at least two components. A first component of the dental material contains the salt of a CH-acidic compound, and an additional component contains an acid with acidity greater than that of the CH-acidic compound of the first component. Both components contain radically polymerizable monomers. When the two components are mixed, the acid of the second component converts the salt of the CH-acidic compound of the first component into a CH-acidic molecule, and the CH-acidic molecule triggers the radical polymerization of the monomers. In addition to the advantages of CH-acidic compounds in dental materials on the basis of a reactive resin, the invention achieves long-term storage stability as a result of an increase in the proportion of the reactive resin matrix in polymerizable dental materials.

21 Claims, No Drawings

POLYMERIZABLE DENTAL MATERIAL

This application is a Continuation of U.S. patent application Ser. No. 12/308,309, filed Jul. 9, 2009, now issued as U.S. Pat. No. 8,883,876, which is a National Stage application under 35 U.S.C. §371 of International Application No. PCT/EP2007/004207, filed May 11, 2007, which claims priority to European Application Ser. No. 06013589.4, filed Jun. 30, 2006.

The invention relates to a polymerizable dental material and to the use of salts of a CH-acid compound.

Chemically curing polymerizable dental materials (frequently also called self-curing or autocatalyzed dental materials in the literature) comprise polymerizable monomers, the polymerization of which is initiated by radicals formed at the start. These radicals are formed through the reaction of a suitable initiator molecule, which on its own has a satisfactory stability on storage at ambient temperature, with a coinitiator. Since this reaction begins immediately after bringing together initiator and coinitiator, both components of the initiator system have to be accommodated separately for the storage of the dental materials. This accordingly results in multicomponent systems, in contrast to light-curing materials, in which the radicals are formed only by illuminating with the blue component of visible light. The components are brought into contact with one another only immediately before the processing of the material and are intimately mixed with one another. This mixing can in this connection be carried out either by hand, using a mixing spatula, or by a self-mixing system (double cartridge with static or dynamic mixing cannulas).

A most frequently used initiator system with chemically curing dental materials in the state of the art consists of a for the most part aromatic amine and an organic peroxide, such as, e.g., described in DE-C-97 50 72. The necessary radicals are formed in this system via a redox reaction between amine and peroxide.

A major disadvantage of the amine/peroxide systems is the generally poor color stability. This originates from products of the initiator components, formed in parallel, side and consecutive reactions, which because of their structure are frequently colored. Those colored compounds can be produced in the radical formation which are formed during the storage of the pastes or are observed in the cured material, for example through the action of visible or UV light (e.g., A. Schmidt: "Kaltpolymerisate: Ein Bericht über ihre Eigenschaften, Einsatzmöglichkeiten and Vorteile" [Cold polymers: A report on their Properties, Possible Uses and Advantages], Dentallabor, 11 [1970], pp. 17-22). This disadvantage cannot, with the amine/peroxide systems, even be removed through the perfectly normal addition of special light and UV stabilizers. For highly esthetic care purposes, these discolorations are disturbing or unacceptable to the patients. Accordingly, for care purposes in the smile region, recourse is frequently had to a great deal of more extravagant and more expensive ceramic (veneers, crowns, bridges, inter alia).

An additional disadvantage of the amine/peroxide system is the toxic and allergenic action of the components of the initiator system and of the reaction and decomposition products thereof. During the curing process, these components can have a direct toxic action. In addition, after the curing, relevant non-copolymerized molecules can be washed out by the acidic saliva. Allergic reactions resulting for a number of patients limit or exclude the use of plastics. In isolated cases, the toxic action can trigger anaphylactic (allergic) shock, which can definitely assume life-threatening forms.

The increase in temperature in the polymerization due to the exothermic reaction process is also problematic. Amine/peroxide-initiated systems polymerize comparatively quickly and thus already have, at the gel point, a very high degree of crosslinking (reaction at double bonds) which releases a relatively high amount of heat from the exothermic reaction. The result is high maximum temperatures. However, an excessively high temperature can result in pulp damage up to the decay of the tooth.

An alternative initiator system, which has a more favorable temperature development and a markedly better color stability, uses CH-acid compounds in combination with divalent transition metal ions and chloride ions. Relevant CH-acid compounds have been intensively investigated by H. Bredereck and his coworkers (H. Bredereck et al.: "Über CH-Aktive Polymerisationsinitiatoren XIII. Mitt. Polymerisationen und Polymerisationsinitiatoren" [CH-Active Polymerization Initiators—XIIIth Communication. Polymerizations and Polymerization Initiators], Makromolekulare Chemie, 92 [1966], pp. 70-90; H. Bredereck et al.: "Polymerisationen und Polymerisationsinitiatoren—16. Einfluβ von Thio-Gruppen in Barbitursäurederivaten auf die Polymerisationsauslösung von Methacrylsäure-methylester" [Polymerizations and Polymerization Initiators—16. Influence of Thio Groups in Barbituric Acid Derivatives on the Initiation of the Polymerization of Methyl Methacrylate], Makromolekulare Chemie, 176 [1975], pp. 1713-1723). Of the CH-acid compounds, barbituric acid derivatives have proven to be convenient in the dental field. They can be prepared in high yields with high purities, are available industrially (Chemische Fabrik Berg GmbH, Mainthalstr. 3, D-06749, Bitterfeld, Germany) and make it possible, through their reaction kinetics, for advantageous properties to be obtained.

The synthesis of barbituric acid derivatives is known, e.g. from E. Fischer and A. Dilthey: "Über c-Dialkylbarbitursäuren und über die Ureide der Dialkylessigsauren" [C-Dialkylbarbituric Acids and the Ureides of Dialkylacetic Acids], Ann., 335 [1904], p. 335), and describes the alkaline condensation of diethyl malonate derivatives with N-substituted urea in sodium alkoxide. The sodium salts of the barbituric acid derivatives obtained in this connection are subsequently converted to the barbituric acid derivatives through the addition of an acid, e.g. of hydrochloric acid.

With the initiator system based on barbituric acid or the derivatives thereof, the barbituric acid derivatives have to be kept separately from the polymerizable monomers. The reason for this is that CH-acid compounds, such as the derivatives of barbituric acid, already form hydroperoxides through autoxidation by atmospheric oxygen, without the participation of Cu(II) and chloride ions. These hydroperoxides decompose with the formation of radicals which initiate the polymerization of the reactive monomers, so that spontaneous polymerization occurs within a short time. This spontaneous polymerization process can be delayed or suppressed for a short time (in the region of a few hours) by the addition of stabilizers but not over a longer period of time, as is desirable with systems stable on storage.

The state of the art is here the replacement of reactive resins in the initiator paste by those which, under dental conditions, cannot be polymerized by CH-acid compounds or by compounds not comprising double bonds (e.g., polyethylene glycol).

The spatial separation of polymerizable monomers and CH-acid barbituric acid derivatives which is required limits the proportion of the polymerizable monomers in the dental material. For flowable materials, which are overridingly applied from conventional double cartridge systems, the addition of unreactive monomers can be at least decreased by reducing the addition of this paste component (mixing ratios of 2:1, 4:1 and 10:1). For these reasons, barbituric acid derivatives in combination with $Cu^{2+}$ and $Cl^-$ are at present exclusively used with the flowable provisional crown and bridge materials which are automatically metered and mixed. Admittedly, the relatively low amount of nonpolymerizing monomers added through the initiator paste also acts as lubricant, which results in a worsening in the mechanical properties (compressive strength, flexural strength, hardness, and the like) and in an increase in the lubricating film.

High viscosity materials, such as, e.g., plastic chemically curing filling composites, are not applicable from cartridge systems and cannot be automatically mixed. They are accommodated in composite syringes or packs and mixed by hand. Metering is carried out by the dentist exclusively by eye. Metering aids have hitherto not been successful. Since equal amounts of material can be better evaluated than, e.g., 10:1, these materials are applied exclusively in the mixing ratio of 1:1. This mixing ratio can be better evaluated by the dentist than unequal ratios and thus result in substantially smaller metering errors and accordingly in better qualities of the material. Although the CH-acid barbituric acid derivatives result in considerably better color stabilities than amine/peroxide systems, these systems are hitherto closed to filling and facing materials because of the high addition of nonpolymerizing monomers and the accordingly concomitant worsening in the mechanical properties.

It is an object of the present invention to create an initiator system for polymerizable dental materials which avoids the disadvantages known from the state of the art and in addition can be used as filling and facing plastics even in materials metered in a ratio of 1:1.

The invention solves this problem by a polymerizable dental material of at least two components which comprises the following components:
  Component 1, comprising
    a) the salt of a CH-acid compound, the CH-acid compound being able to initiate a radical polymerization,
  Component 2, comprising
    b) an acid, the acid strength of which is greater than that of the CH-acid compound present as salt in the in component 1,
the component 1 and the component 2 of the polymerizable dental material comprising monomers which can polymerize under radical conditions.

The essence of the invention is that, in contrast to the initiator systems based on CH-acid compounds of the state of the art, use is made of a precursor of the active initiator molecule, namely a salt of the CH-acid compound. The CH-acid compound is only released after the addition of an acid, the acid strength of which is greater than that of the CH-acid compound present as salt according to the rule "salt of a weak acid+strong acid gives salt of a strong acid+weak acid", and can subsequently function as initiator molecule for the process for the polymerization of the monomers.

The invention has recognized that, in contrast to the CH-acid compounds, such as those used in the initiator systems of the state of the art, the salt of the CH-acid compound is also stable on storage over relatively long periods of time. Accordingly, the initiator activity for the polymer reaction of the polymerizable monomers is also guaranteed with relatively long storage of the components, of the polymerizable dental material. According to a preferred embodiment of the invention, the pastes from which the polymerizable dental material is mixed, and in particular the paste comprising the salt of the CH-acid compound, are stable with regard to color and/or shelf life for more than 3 months, preferably more than 6 months, particularly preferably more than 24 months.

The invention has furthermore recognized that, starting from the initiator system according to the invention, according to a preferred embodiment of the invention, polymerizable monomers can be introduced into both components of the dental material. Accordingly, the undesirable limitation explained at the start on the amount of polymerizable monomers in the polymerizable dental material, i.e. the proportion of the polymer matrix in the dental material, can be lifted. This also results in advantageous mechanical properties of the polymerized dental material since the amount of the unreactive monomers (e.g., monomers with unreactive double bonds or compounds not comprising double bonds), which are usually added for reasons of the handleability of the initiator paste (e.g., for adjusting pasty properties in order to be able to use the paste in cartridge systems), can be reduced or entirely dispensed with. It is known that noncopolymerizing resins or fillers in the base and initiator pastes act as lubricants and, depending on the content, disadvantageously affect the mechanical properties. This effect is to the greatest possible extent avoided by the use of the initiator system according to the invention, in which, according to a preferred embodiment of the invention, the monomers of the two components polymerize under radical conditions when they are mixed.

Monomers which can polymerize under radical conditions which are preferred according to the invention are chosen from the group consisting of acrylate esters and methacrylate esters.

The polymerizable dental material according to the invention preferably comprises a total of more than 50% by weight, preferably more than 60% by weight, more preferably more than 70% by weight, more preferably more than 80% by weight, more preferably more than 90% by weight, more preferably more than 95% by weight, more preferably more than 98% by weight, of monomers which can polymerize under radical conditions. According to a preferred embodiment of the invention, the component 1 of the polymerizable dental material comprises more than 50% by weight, preferably more than 60% by weight, more preferably more than 70% by weight, more preferably more than 80% by weight, more preferably more than 90% by weight, more preferably more than 95% by weight, more preferably more than 98% by weight, of monomers which can polymerize under radical conditions. According to a preferred embodiment of the invention, the component 1 and/or the component or the polymerizable dental material in total does not comprise any monomer which cannot polymerize under radical conditions.

The polymerizable dental material according to the invention can comprise the component 1 in a first paste and the component 2 in a second paste and can be mixed in a designated mixing ratio of the two pastes of 1:10 or greater, preferably 1:4 or greater, more preferably 1:2 or greater, particularly preferably 1:1.

Suitable as salt of the CH-acid compound of the component 1 are in particular salts of α-benzoylpropionitriles, α-cyanocarboxylic acid esters, α-cyanocarboxamides, cyclic β-oxonitriles, β-diketones, cyclic β-diketones, cyclic β-oxocarboxylic acid esters, cyclic β-oxolactones, malonic acid, malonic acid derivatives, pyrazole derivatives, barbituric acid or barbituric acid derivatives.

The salt of the CH-acid component is preferably a salt chosen from the group consisting of monovalent and divalent salts of alkali metal and alkaline earth metal ions. The salt of the CH-acid compound can for example be a sodium salt.

Use may be made of an organic or inorganic acid as acid of the component 2 within the meaning of the present invention, provided that the acid strength thereof is greater than that of the CH-acid compound present as salt in the component 1.

Non-oxidizing acids, such as, e.g., hydrochloric acid or phosphoric acid, are suitable as inorganic acids.

Particularly suitable organic acids are monocarboxylic acids chosen from the group consisting of formic acid, acetic acid and benzoic acid and derivatives of these acids or dicarboxylic acids chosen from the group consisting of oxalic acid, malonic acid, succinic acid, adipic acid, pimelic acid, azelaic acid, sebacic acid, maleic acid, fumaric acid, sorbic acid, phthalic acid and terephthalic acid and derivatives of these acids or tricarboxylic acids chosen from the group consisting of hemimellitic acid, trimellitic acid, trimesic acid, agaric acid, citric acid, 1,2,3-propanetricarboxylic acid and derivatives of these acids or multicarboxylic acids chosen from the group consisting of pyromellitic acid and mellitic acid and derivatives of these acids or polycarboxylic acids chosen from the group consisting of polyacrylic acid and polymethacrylic acid and derivatives of these acids.

The $pK_a$ value, which refers to the dissociation equilibrium in an aqueous medium, can in this connection be brought in as a measure of the CH-acidity in addition to other factors. A choice of organic acids within the meaning of the present invention, the $pK_a$ values of which are smaller than the $pK_a$ value of barbituric acid (4.01), is for example 2,5-dihydroxybenzoic acid (2.97), fumaric acid (3.03), maleic acid (1.83), phthalic acid (2.89), salicylic acid (2.97), 2,4,6-trihydroxybenzoic acid (1.68) and cinnamic acid (3.89).

The polymerizable dental material according to the invention can comprise, in at least one of the components of the polymerizable dental material, transition metal cations, preferably $Cu^{2+}$ ions, and anions suitable for radical formation, preferably halide ions, more preferably chloride ions, which initiate, control and accelerate the polymerization process. The anions suitable for radical formation, preferably halide ions, more preferably chloride ions, and the transition metal cations, preferably $Cu^{2+}$ ions, which optionally belong to the initiator system, are preferably present in the base paste (component 1) of the claimed polymerizable dental material but can, according to requirements, also be added to the initiator paste (component 2).

The dental material according to the invention can comprise fillers in at least one of the components. The fillers used according to the invention are preferably nano- and/or microscale (in some cases radio-opaque) fillers, preferably glass powders, glass ceramic powders, metal, semi-metal or mixed metal oxides, silicate, nitride, sulfate, titanate, ziconate, stannate, tungstate or silicon dioxide compounds or a mixture of these compounds or spherical fillers, quartz powders or a mixture of these powders or filler-comprising or filler-free splinter polymers and/or bead polymers. The nanoscale fillers used according to the invention are particularly preferably silicon dioxide, aluminum oxide, zirconium dioxide, titanium dioxide, zinc oxide, tin dioxide, cerium oxide, aluminum/silicon oxides, silicon/zinc oxides, silicon/zirconium oxides, iron oxides and the mixtures thereof with silicon dioxide, indium oxides and the mixtures thereof with silicon dioxide and/or tin dioxide, boron nitride, strontium sulfate, barium sulfate, strontium titanate, barium titanate, sodium zirconate, potassium zirconate, magnesium zirconate, calcium zirconate, strontium zirconate, barium zirconate, sodium tungstate, potassium tungstate, magnesium tungstate, calcium tungstate, strontium tungstate and/or barium tungstate.

According to a preferred embodiment of the invention, the filler can be a surface-modified filler, preferably an organically surface-modified filler. Depending on its surface modification, for example a silanization, the filler can have functional groups, for example reactive methacrylate groups, on its surface which can react chemically, preferably under radical conditions, with the monomers or exhibit a high affinity for the polymer matrix formed from the monomers.

The dental material according to the invention can, for adjusting certain properties, additionally comprise "additives" or "modifiers". Some examples, which do not limit the general nature, are mentioned below: inorganic and/or organic color pigments or dyes, stabilizers (such as, e.g., substituted and unsubstituted hydroxyaromatic compounds, tinuvins, terpinenes, phenothiazine, "HALS"—Hindered Amine Light Stabilizers—and/or heavy metal scavengers, such as EDTA), plasticizers (such as, e.g., polyethylene glycols, polypropylene glycols, unsaturated polyesters, phthalates, adipates, sebacates, phosphoric acid esters, phosphonic acid esters and/or citric acid esters), ion-releasing substances, in particular those which release fluoride ions (such as, e.g., sodium fluoride, potassium fluoride, yttrium fluoride, ytterbium fluoride and/or quaternary ammonium fluorides), bactericidal or antibiotically effective substances (such as, e.g., chlorhexidine, pyridinium salts, penicillins, tetracyclines, chloramphenicol, antibacterial macrolides and/or polypeptide antibiotics) and/or solvents (such as, e.g., water, acetone, ethanol, isopropanol, butanone and/or ethyl acetate).

The dental material according to the invention can be used for prosthetic, preservative and preventive dentistry. Without claiming to be complete, some sample applications may be mentioned by way of representation: filling material, stump buildup material, fixing material, material for temporary and permanent crowns and bridges, bonding materials, material for dental technology for the preparation of inlays, onlays, veneers, artificial teeth, cast materials, fissure sealing material and root canal sealing material.

The invention is illustrated below with exemplary embodiments without limiting the general nature.

Example 1

Synthesis of the Sodium Salt of 1,3,5-trimethylbarbituric Acid

The synthesis has been described by A. C. Cope et al., "1,3-Dimethyl-5-alkyl Barbituric Acids", J. Amer. Chem. Soc., 63, 365 (1941). 0.1 mol (=17.420 g) of diethyl methylmalonate were added to 97.214 g of 21% sodium alkoxide solution in ethanol (=0.3 mol of sodium alkoxide) and the two components were intimately mixed with one another. In this connection, the sodium salt of diethyl methylmalonate and ethanol are formed. Subsequently, 0.1 mol (=8.811 g) of N,N-dimethylurea was dissolved in 15 ml of ethanol (analytical grade) and slowly added dropwise to the solution, resulting in the sodium salt of 1,3,5-trimethylbarbituric acid. Subsequently, the batch was heated at reflux for 11.5 hours.

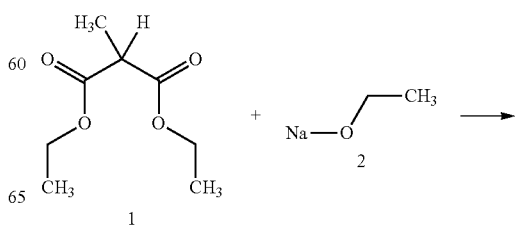

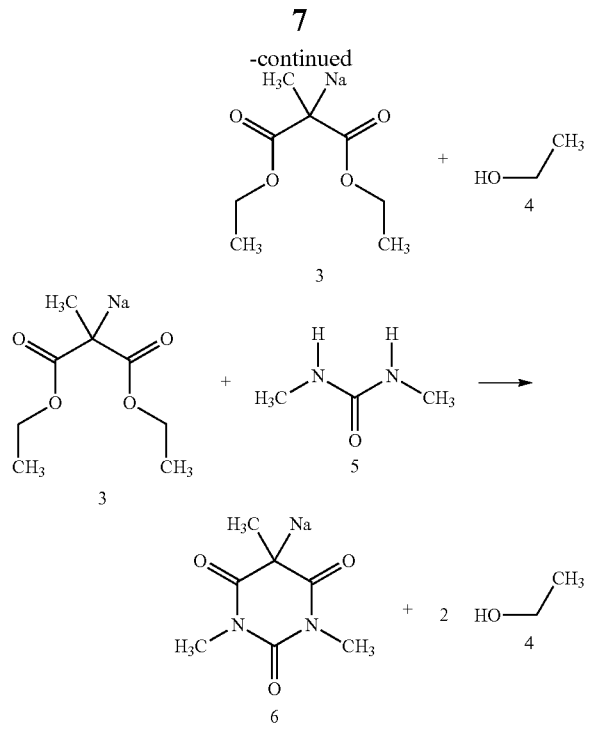

1 = Diethyl methylmalonate
2 = Sodium alkoxide
3 = Sodium salt of diethyl methylmalonate
4 = Ethanol
5 = N,N-Dimethylurea
6 = Sodium salt of 1,3,5-trimethylbarbituric acid The solution was concentrated to dryness on a rotary evaporator and the residue was taken up in 100 ml of deionized water. The solution was then extracted five times by shaking each time with 20 ml of ether. The aqueous phase was again concentrated to dryness on a rotary evaporator and subsequently transferred onto a Büchner funnel. The residue was washed here with isopropanol until the isopropanol being sucked off no longer exhibited any coloring. Since the solid was still colored slightly brownish, it was washed with a small amount of ethanol (analytical grade) until the ethanol also no longer exhibited any coloring.

The purity was determined by means of HPLC to be 99.59%. The yield was 65.30%.

Example 2

Preparation and Stability on Storage of the Initiator Paste

Three different initiator pastes were prepared and were investigated for their stability on storage at ambient temperature and at 40° C.

Paste 1: Paste comprising, as fillers, polyethylene glycol with an average molecular weight of 400 g/mol (PEG 400), as unreactive resin component, and dental glass, which was surface-treated with silane not comprising methacrylate groups, and which comprised 1,3,5-trimethylbarbituric acid as initiator molecule.

Paste 2: Paste comprising, as fillers, methacrylates and dental glass, which was surface-treated with silane carrying methacrylate groups, and which comprised 1,3,5-trimethylbarbituric acid as initiator molecule.

Paste 3: Paste comprising, as fillers, methacrylates and dental glass, which was surface-treated with silane carrying methacrylate groups, and which comprised the sodium salt of 1,3,5-trimethylbarbituric acid as initiator molecule.

The formulations for the pastes are shown in the following table. In this connection, the amount of initiator molecule added was calculated so that all three pastes comprised the same number of moles.

| Constituent | Paste 1 % by weight | Paste 2 % by weight | Paste 3 % by weight |
| --- | --- | --- | --- |
| Bis-GMA | — | 37.2179 | 36.9790 |
| TEDMA | — | 16.7211 | 16.6138 |
| PEG 400 | 53.9390 | — | — |
| Aerosil R812 | 1.5000 | 1.5000 | 1.4904 |
| Dental glass sil. without methacrylate groups | 39.9350 | — | — |
| Dental glass sil. with methacrylate groups | — | 39.9350 | 39.6785 |
| 1,3,5-Trimethylbarbituric acid | 4.6260 | 4.6260 | — |
| Sodium salt of 1,3,5-Trimethylbarbituric acid | — | — | 5.2383 |

In order to obtain evidence with regard to the stability on storage of the pastes, the pastes were stored at ambient temperature and at 40° C. and examined at regular intervals for polymerized constituents. While paste 2 was already completely polymerized after 90 min, pastes 1 and 3 show not even the slightest signs of polymerization even after more than 6 months. This shows that pastes with reactive monomers and 1,3,5-trimethylbarbituric acid as active initiator molecule are not stable on storage, while pastes which are stable on storage result when the sodium salt of 1,3,5-trimethylbarbituric acid is used as precursor of the active initiator molecule 1,3,5-trimethylbarbituric acid.

Example 3

Investigation of the Reactivity of the Initiator Pastes from Example 2

In order to investigate the reactivity of the initiator pastes prepared in example 2, these were mixed by hand with the base paste of the product Luxatemp Automix A2 from DMG Hamburg in the ratio 10:1 (10 parts of base paste, 1 part of initiator paste) and the setting time was determined.

With paste 1, which comprises polyethylene glycol, the setting began after 1:40 min and was complete after 3:20 min. This means that this paste is stable on storage and reactive.

When the initiator paste 2 is used, setting begins at 1:50 min and is here likewise complete after approximately 3:20 min. That is, the paste has a satisfactory reactivity but is not, as shown in example 2, stable on storage. It accordingly cannot be used as initiator paste.

The initiator paste 3, which comprises reactive methacrylate groups and the sodium salt of 1,3,5-trimethylbarbituric acid, did not set, as expected, after mixing with the above-mentioned base. One drop of 32% hydrochloric acid was therefore added to the mixed system (0.6 g of base paste+0.06 g of initiator paste). The material polymerized after 55 min.

Example 4

Reaction of the Initiator Paste 3 from Example 2 with Hydrochloric Acid or a Base Paste Comprising Hydrochloric Acid The initiator paste 3 from example 2, which comprises the sodium salt of 1,3,5,-trimethylbarbituric acid and reactive methacrylate monomers, was mixed with one drop of hydrochloric acid. The paste was cured after approximately 90 minutes.

In a second experiment, the reactive base paste of the product Luxatemp Automix from DMG Hamburg, comprising reactive methacrylate monomers and coinitiators, was mixed with the initiator paste 3 from example 2, in addition to the drop of hydrochloric acid, in the ratio 1:1 to the initiator paste. The paste obtained polymerized after 20 minutes.

The experiments verify that the sodium salt of the barbituric acid derivative is converted in situ into the free acid after addition of the hydrochloric acid and, after build up of the CH-acidity, the pastes polymerize after a short time as a result of the subsequent autoxidation. The experiments furthermore show that the polymerization times can be considerably shortened by coinitiators present in the base paste, for example alkylammonium chlorides and Cu(II) compounds, such as are present in the base paste of the product Luxatemp Automix.

Example 5

Reaction of the Initiator Paste 3 from Example 2 with Organic Acids

A selection of organic acids, the $pK_a$ values of which are lower than that of barbituric acid, were tested for their ability to convert the sodium salt of the paste 3 according to example 2 to the free 1,3,5-trimethylbarbituric acid. The setting time of the paste mixture was used as measure of the convertibility. The concentrations of the organic acids used were calculated so that they were equimolar, in a mixing ratio of 10:1, to the number of moles of the initiator molecule used in the initiator paste. On mixing the initiator paste with the organic acids mentioned below:
2,5-dihydroxybenzoic acid,
fumaric acid,
maleic acid,
phthalic acid,
salicylic acid,
2,4,6-trihydroxybenzoic acid and
cinnamic acid,
geling, i.e. polymerization, could be observed within 30 minutes.

This may be described subsequently by way of example for the reactivity of the initiator paste 3 from example 2 after addition of fumaric acid or 2,5-dihydroxybenzoic acid.

0.5 g of the base paste mentioned above was mixed with 0.05 g of the initiator paste 3 from example 2 and one drop of fumaric acid dissolved in hydroxyethyl methacrylate (0.1 g in 10 ml) was added. The material polymerized after 6 minutes.

In an additional experiment, the fumaric acid solution was now incorporated in the base paste. In this connection, a molar ratio of fumaric acid:sodium salt of 1,3,5-trimethylbarbituric acid of 1:1 (after mixing the pastes in the ratio of 10:1) was set. The material polymerized after 19 minutes.

In an additional experiment, use was made of 2,5-dihydroxybenzoic acid, which has a better solubility in hydroxyethyl methacrylate. For this, 0.1 g of the 2,5-dihydroxybenzoic acid was dissolved in 1 ml of hydroxyethyl methacrylate. One drop of the solution (0.0248 g) was incorporated in 0.5 g of the abovementioned base paste. Subsequently, 0.05 g of the initiator paste 3 from example 2 was added and thoroughly mixed in. The paste mixture was set after 9 min.

Example 6

According to the Invention

In order to investigate the reactivity and the flexural strength as measure of the mechanical strength of the dental material according to the invention, the initiator paste 4 specified below was prepared and mixed in the ratio 1:1 with the base paste from example 3, in which 1.53% by weight of 2,5-dihydroxybenzoic acid had been incorporated.

| Constituent | Paste 4 % by weight |
|---|---|
| Bis-GMA | 38.5 |
| TEDMA | 17.1 |
| PEG 400 | — |
| Aerosil R812 (surface-treated pyrogenic silica) | 1.6 |
| Dental glass sil. with methacrylate groups (D50: 1.5 µm) | 42.1 |
| 1,3,5-Trimethylbarbituric acid | — |
| Sodium 1,3,5-trimethylbarbiturate | 0.7 |

The setting began after 2:30 min and was complete after 5:30 min. The mean flexural strength was 72.11 MPa (+/− 6.00, 10 measurements). The maximum flexural strength was 81.97 MPa.

Example 7

Comparative Example

In order to investigate the flexural strength of a dental material not according to the invention, the initiator paste 5 specified below was prepared and mixed with the base paste from example 3 in the ratio 1:1.

| Constituent | Paste 5 % by weight |
|---|---|
| Bis-GMA | — |
| TEDMA | — |
| PEG 400 | 56.1 |
| Aerosil R812 (surface-treated pyrogenic silica) | 1.6 |
| Dental glass sil. without methacrylate groups (D50: 1.5 µm) | 41.5 |
| 1,3,5-Trimethylbarbituric acid | 0.8 |
| Sodium 1,3,5-trimethylbarbiturate | — |

The mean flexural strength of the cured dental material was 16.89 MPa (+/−2.25, 10 measurements) and the maximum flexural strength was 19.03 MPa.

The flexural strength of the dental material of example 6 according to the invention, with a mean flexural strength of 72.11 MPa and a maximum flexural strength of 81.97 MPa, accordingly clearly lay above the corresponding values of comparative example 7 and verifies the extreme load-bearing capacity of the dental material according to the invention.

What is claimed is:

1. A syringe or cartridge system for providing equal amounts of separate components of a polymerizable dental material, wherein said syringe or cartridge system contains:
   a) an amount of an unpolymerized first component comprising:
      i) a salt of a CH-acid compound, wherein said CH-acid compound has an acid strength and is able to initiate a radical polymerization, and
      ii) monomers polymerizable under radical conditions,
   wherein said first component is stable on storage at ambient temperature for more than 3 months; and b) an amount of an unpolymerized second component comprising:
   i) an acid having an acid strength that is greater than the acid strength of the CH-acid compound present as a salt in said first component, and
   ii) monomers polymerizable under radical conditions;
wherein said first component and said second component contained in said syringe or cartridge system are not in contact, and wherein said syringe or cartridge system is configured to automatically meter and mix said first component and said second component in a ratio of 1:1.

2. The syringe or cartridge system of claim 1, further comprising a mixing cannula.

3. The syringe or cartridge system of claim 2, wherein said mixing cannula is selected from a static mixing cannula and a dynamic mixing cannula.

4. The syringe or cartridge system of claim 1, wherein at least 50% by weight of monomers polymerizable under radical conditions present in the total weight of said equal amounts of said first component and said second component are in said first component.

5. The syringe or cartridge system of claim 1, wherein said first component or said second component, or both, contain substantially no monomer that cannot polymerize under radical conditions.

6. The syringe or cartridge system of claim 1, wherein monomers in said first component are polymerizable under radical conditions with monomers in said second component upon mixing of said first component and said second component.

7. The syringe or cartridge system of claim 1, wherein the salt of the CH-acid compound of said first component is selected from the group consisting of salts of α-benzoylpropionitriles, α-cyanocarboxylic acid esters, α-cyanocarboxamides, cyclic β-oxonitriles, βdiketones, cyclic β-diketones, cyclic β-oxocarboxylic acid esters, cyclic β-oxolactones, malonic acid, malonic acid derivatives, pyrazole derivatives, barbituric acid or barbituric acid derivatives.

8. The syringe or cartridge system of claim 1, wherein the salt of the CH-acid compound of said first component is a salt selected from the group consisting of monovalent and divalent salts of alkali metal and alkaline earth metal ions.

9. The syringe or cartridge system of claim 1, wherein the acid of said second component is an inorganic acid.

10. The syringe or cartridge system of claim 1, wherein the acid of said second component is an organic acid.

11. The syringe or cartridge system of claim 10, wherein the organic acid is selected from the group consisting of formic acid, acetic acid, benzoic acid, oxalic acid, malonic acid, succinic acid, adipic acid, pimelic acid, azelaic acid, sebacic acid, maleic acid, fumaric acid, sorbic acid, phthalic acid, terephthalic acid, hemimellitic acid, trimellitic acid, trimesic acid, agaric acid, citric acid, 1,2,3-propanetricarboxylic acid, pyromellitic acid, mellitic acid, polyacrylic acid, polymethacrylic acid and derivatives of these acids.

12. The syringe or cartridge system of claim 1, wherein said monomers polymerizable under radical conditions in said first component are selected from the group consisting of acrylate esters and methacrylate esters.

13. The syringe or cartridge system of claim 1, wherein said monomers polymerizable under radical conditions in said second component are selected from the group consisting of acrylate esters and methacrylate esters.

14. The syringe or cartridge system of claim 1, wherein said first component further comprises a transition metal cation and an anion suitable for radical formation, thereby creating an accelerative first component.

15. The syringe or cartridge system of claim 1, wherein said second component further comprises a transition metal cation and an anion suitable for radical formation, thereby creating an accelerative second component.

16. The syringe or cartridge system of claim 1, wherein at least one of said first and said second components further comprises a filler selected from the group consisting of micro- and nanoscale fillers.

17. The syringe or cartridge system of claim 16, wherein said filler is surface-modified filler.

18. The syringe or cartridge system of claim 17, wherein said surface-modified filler has, on its surface, functional groups that can react chemically with monomers in said polymerizable dental material, or that have a high affinity for a polymer matrix formed from monomers in said polymerizable dental material.

19. The syringe or cartridge system of claim 18, wherein said surface-modified filler is surface-modified with silane carrying reactive groups selected from the group consisting of acrylate or methacrylate.

20. A method of providing a polymerized dental material selected from the group consisting of a filling material, stump buildup material, fixing material, bonding material, material for temporary and permanent crowns and bridges, material for dental technology for the preparation of inlays, onlays, veneers, artificial teeth, cast materials, fissure sealing material and root canal sealing material, comprising dispensing a first component and a second component from a syringe or cartridge system of claim 1, wherein said first component and said second component are metered and mixed in a ratio of 1:1, and wherein said monomers polymerizable under radical conditions polymerize.

21. The syringe or cartridge system of claim 1, wherein at least one of the components of said first component and said second component further comprises a modifier or other additive.

* * * * *